United States Patent [19]
Niklason et al.

[11] Patent Number: 5,506,877
[45] Date of Patent: Apr. 9, 1996

[54] MAMMOGRAPHY BREAST COMPRESSION DEVICE AND METHOD

[75] Inventors: Loren T. Niklason, Beverly; Lynne Jameson-Meehan, Melrose; Daniel B. Kopans, Waban; Richard Moore, Concord, all of Mass.

[73] Assignee: The General Hospital Corporation, Boston, Mass.

[21] Appl. No.: 344,284

[22] Filed: Nov. 23, 1994

[51] Int. Cl.⁶ ..................................................... A61B 6/04
[52] U.S. Cl. ............................................. 378/37; 378/208
[58] Field of Search ............................ 378/37, 204, 208, 378/177

[56] References Cited

U.S. PATENT DOCUMENTS

| | | | |
|---|---|---|---|
| 3,556,081 | 1/1971 | Jones | 378/37 X |
| 3,971,950 | 7/1976 | Evans et al. | 378/37 |
| 4,658,409 | 4/1987 | Summ | 378/37 |
| 4,962,515 | 10/1990 | Kopans | 378/37 |
| 5,029,193 | 7/1991 | Saffer | 378/37 |
| 5,040,198 | 8/1991 | Hixson, Sr. | 378/37 |
| 5,050,197 | 9/1991 | Virta et al. | 378/37 |
| 5,305,365 | 4/1994 | Coe | 378/37 |

OTHER PUBLICATIONS

MAM–CP TILT–MAG Addendum, Maintenance Manual, 9092.410, (Preliminary) Continental X–Ray Corporation, Broadview, Illinois, 1993.

The Planmed Sophie, Product Brochure No Date.

The Contour Mammography System, Product Brochure Bennett X–Ray Technologies, Copyright 1992 Bennett X–Ray Corporation, 445 Oak Street, Copaigue, NY 11726.

*Primary Examiner*—David P. Porta
*Attorney, Agent, or Firm*—Meltzer, Lippe, Goldstein et al.

[57] ABSTRACT

A breast compression device is disclosed for use in a mammography system. A paddle support frame is provided which is slidably connected to a system arm of the mammography system. The paddle support frame is located between the x-ray tube and the detector of the mammography system. A compression paddle is pivotally connected within the support frame by a pivot connection. The pivot connection is located on a chest wall side of the support frame. The chest wall side is opposite the system arm. The compression paddle is substantially horizontal to the detector and is rotatable around the pivot connection. The compression paddle may include a breast portion which is substantially parallel to the detector and a chest wall portion which is substantially vertical to the detector. The compression paddle may also have a contoured shape where the chest wall portion is angled away from the system arm and the breast portion is contoured to mimic the contours of the breast.

35 Claims, 5 Drawing Sheets

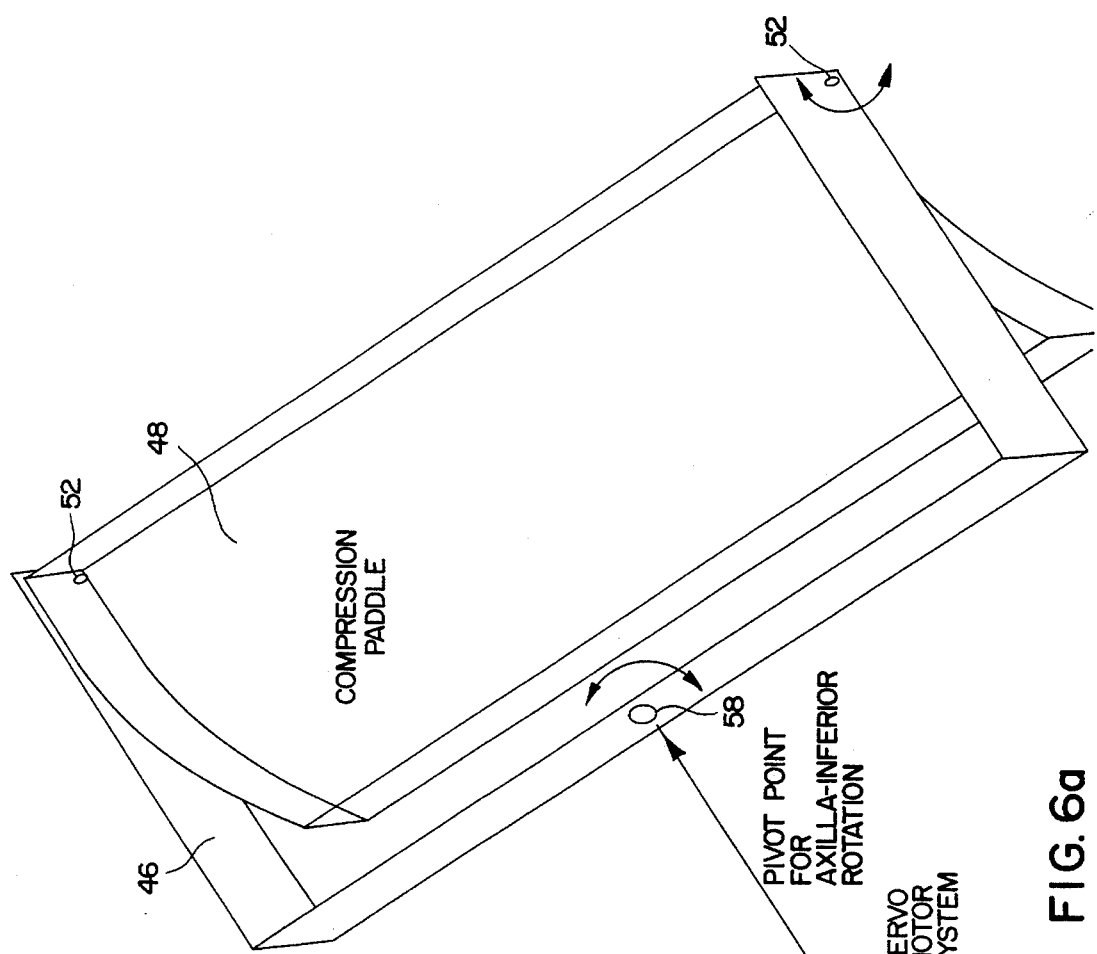
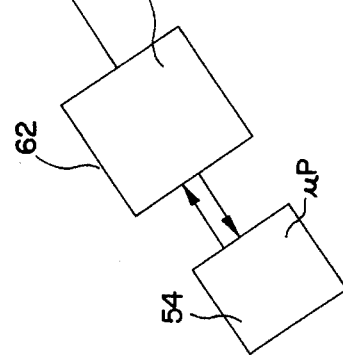
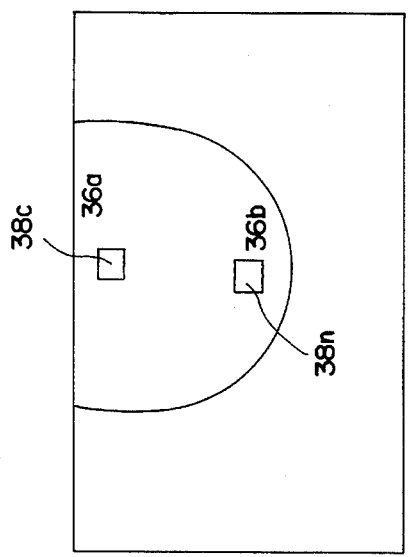
FIG. 6a
FIG. 5b

MAMMOGRAPHY BREAST COMPRESSION DEVICE AND METHOD

FIELD OF THE INVENTION

This invention relates to a mammography breast compression device and method. It specifically relates to such a compression device which results in more uniform compression and increased compression force on the breast.

BACKGROUND OF THE INVENTION

In mammography systems, a compression device, such as a compression paddle, is used to compress the breast of a patient. Firm compression of the breast is essential for good quality mammography. Firm compression spreads out the breast structures, thereby reducing superimposed structures. Current breast compression devices compress the breast with the compression paddle being parallel to the image detector. For the craniocaudal view, these devices often provide good compression of the breast near the chest wall but inadequate compression toward the nipple. For the mediolateral view, current breast compression devices may not provide good compression for both the axilla and inferior or main breast. Such parallel compression devices provide roughly uniform tissue thickness. However, the breast is compressed with more force where the breast is thicker and less force where the breast is thinner. Therefore, in areas where the breast is thinner and compressed with less force, the image quality will be poor. A conventional mammography system is disclosed in U.S. Pat. No. 5,305,365 to Coe. This patent is hereby incorporated by reference.

FIG. 1 illustrates the regions of the breast as viewed from the superior or cranial side. The axillary tail 1 is located towards the armpit or axilla. The posterior 2, middle 3, anterior 4 and subareolar 5 make up the main lobe of the breast.

There are two standard views of the breast taken for a mammogram. FIG. 2a illustrates the mediolateral oblique view of the breast. The direction of the x-ray beam is indicated by arrow 6a. The image detector 7 extends from the axilla portion 8 of the breast to the inferior portion 9 or main lobe of the breast. The x-ray beam first enters the breast through the medial side 10 and exits through the lateral side 11. FIG. 2b illustrates the craniocaudal view of the breast. The direction of the x-ray beam is indicated by arrow 6b. The image detector 7 is placed under the main lobe 9 of the breast. The x-ray beam 6b enters the breast through the cranial or superior portion 12 of the breast and exits through the caudal or inferior portion 13 of the breast. For both of the two standard views, conventional systems do not generate enough compression of the entire breast tissue to provide good quality images for cancer detection. Therefore, using the conventional systems may result in inaccurate diagnoses.

A known compression paddle system which comes down at an angle was produced by Planmed of Helsinki, Finland. Planmed's mammography systems are motorized and can be controlled by foot pedals or switches. This conventional system is a two phase system. The first phase is the compression phase with steady compression. When a preset compression force is reached, an audible signal is given and the second phase of fine tuned compression can be applied. The breast is prepositioned by the technologist. During the first phase of compression, the chest wall side of the upper paddle is angled toward the image detector at the start of compression. As it descends and starts to compress the breast, the paddle begins to level and exert a two-phase force on the breast. At completion of the compression, the paddle is level or parallel to the image detector.

SUMMARY OF THE INVENTION

A main object of this invention is to provide a device which will rotate in several directions to provide more uniform compression for the entire breast and surrounding tissues which are imaged on the mammography detector. The object is not only to obtain more uniform compression but also to place more of the breast and surrounding breast tissue under more compression force and thus improve the image for these areas. Improved compression with this invention may occur anywhere in the imaged tissue and may be at the chest wall, nipple end of the breast, axilla, or the main lobe of the breast. For example, some women have pear shaped breasts with more tissue near the nipple and less near the chest wall. For these women almost no rotation would be necessary toward the nipple, however, the inventive compression device would provide better compression near the chest wall. For other women, the breast is thicker at the chest wall. Therefore, the inventive paddle is rotated towards the nipple to provide increased and more uniform pressure.

The inventive device is part of a mammography system which has an x-ray tube connected to a system arm and an image detector connected the system arm at an end opposite from the x-ray tube. The inventive device comprises a compression device having a pivot point at the chest wall of the patient. A paddle support frame slidably mounted on the system arm between the x-ray tube and the detector is provided. A compression panel or paddle is pivotally connected to a chest wall side of the support frame, that is a side of the support frame which is away from the system arm. The paddle may be locked into position at any degree of rotation. The compression panel is substantially parallel with respect to the detector but is rotatable about the pivot connection on the chest wall side of the support frame.

In one embodiment, the compression paddle has a short, chest wall portion which is substantially perpendicular to the detector and a breast portion which is substantially parallel to the detector and extends over the breast.

In a preferred embodiment of the invention, the compression paddle is shaped so as to push the breast tissue away from the chest wall as the breast is initially compressed. Conventional flat compression plates compress the breast tissue with some breast tissue being pushed toward the chest wall. This breast tissue may be pushed out of the imaged volume of breast tissue. The inventive paddle has a contoured shape. The contoured shape is achieved by making the breast portion of the paddle either gently curved or composed of angled segments. In another embodiment, the chest wall portion of the paddle is angled away from the system arm and in toward the chest wall in such a way that as the paddle is rotated down over the nipple end, the chest wall portion rotates until it is essentially perpendicular to the detector. The contoured shape of the paddle provides increased compression toward the nipple end of the breast, without pushing the breast tissue away from the image detector. Alternatively, the chest wall portion may be hinged so that it remains perpendicular to the detector during rotation.

Initially, the compression device is brought down to the breast parallel to the detector plate. After achieving initial compression of the breast by a straight downward movement, the breast portion of the compression paddle nearest the nipple end of the breast is moved or rotated toward the detector, while the chest wall portion near the chest wall remains in substantially the same position. Advantageously, the effect of this two step compression is to spread out the breast tissue near the nipple end of the breast, which results in less scattered and radiation and improved visibility of detail due to the reduction of superimposed structures. Use of the contoured paddle pushes the breast tissue away from the chest wall and into the imaged volume.

In another embodiment of the invention, an axilla-inferior rotation of the paddle, i.e., rotation towards the axilla or towards the main lobe of the breast is provided. The pivot used for the axilla-inferior rotation can be lockable. The axilla portion of the breast is located near or in the armpit. Such a rotation provides improved compression of the breast in the mediolateral oblique view. In this view, the breast is compressed from high in the axilla to the inferior main lobe of the breast. In many patients, either the axilla region or the inferior breast is not adequately compressed with conventional systems. In the present invention, the compression paddle rotates such that both the axilla region and the inferior breast are under adequate compression.

In one embodiment, the pivot connection and the axilla-inferior connection are lockable for manual rotation of the device. The pivot connection is locked during the initial parallel compression and then unlocked for rotation of the paddle towards the detector at the nipple end. After rotation, the pivot connection would be locked prior to making an x-ray exposure. For axilla-inferior rotation, when the pivot is unlocked, the paddle will rotate on its own.

In another embodiment, the paddle is mounted at the pivot connection with some resistance to rotation. The rotation commences when a predetermined force is achieved during the initial compression. Alternatively, the pivot connection is located along the breast portion of the paddle away from the chest wall portion. The axilla-inferior rotation pivot connection may also be mounted with some resistance, so that its rotation will commence upon the force being greater at the axilla than at the inferior or visa-versa.

In yet another embodiment, the rotation of the paddle is controlled by motors and a microprocessor. The overall compressive force applied during the initial compression is measured by a force sensing system. When this overall force reaches a predetermined level, the microprocessor commences the rotation towards the nipple. The axilla-inferior rotation may also be controlled by a motor system which would sense the force applied to the axilla and inferior ends of the breast.

In one embodiment of the invention, automatic exposure control (AEC) detectors are placed on the radiation exit side of the breast to control x-ray beam shaping. X-ray beam shaping may be accomplished by rotation of the x-ray tube or a radiation filter. In addition, a wedge filter may be used to shape the beam. It may be necessary to shape the beam such that the intensity of the beam changes from nipple to chest wall or from axilla to inferior (main lobe of breast). Current mammography AEC devices use a single radiation detector which may be moved from the chest wall out toward the nipple end of the breast. An AEC with multiple detectors, as in the present invention, would be advantageous for feedback to control beam shaping. An area AEC detector would also be advantageous.

Although x-ray beam shaping may be necessary for filmscreen detection it will not be needed for the majority of digital detectors for mammography that are under development. These detectors will have much wider exposure latitude (range of x-ray exposure which may be imaged with adequate contrast and signal to noise). For these digital detectors, x-ray beam shaping will not be necessary.

Advantages of the inventive device include: improved image quality and reduced radiation dose. The improved image quality is due to higher contrast images with better x-ray penetration and spreading out of the tissue which results in fewer superimposed structures and should improve lesion or microcalcification detection. The reduced radiation dose may increase the safety of the system. The inventive device has been found to be of equal comfort for the patient as the conventional devices.

Breasts composed of mainly fatty tissue are easier to penetrate with x-rays than breasts composed mainly of glandular tissue. Breast cancers are more easily detectable in mammograms of fatty breasts. As the amount of glandular tissue increases in the breast, the breast becomes denser and penetration is more difficult. Superimposed glandular structures may obscure the visibility and hence detection of breast cancer or other lesions. The present invention is advantageous because it spreads the glandular tissue out and allows better penetration, thereby obtaining better cancer or lesion detection due to improved image quality and compressed breast shape. The image quality is further improved by axilla-inferior rotation of the present invention for the mediolateral oblique view. Compression of the entire breast, including the axilla and inferior or main lobe of the breast, is achieved. Further improvement in image quality is realized with the contoured compression shape, which provides more compression of the breast tissue toward the nipple end of the breast. Improved compression also immobilizes the breast, preventing motion during the x-ray exposure.

The contoured paddle has been found to result in major improvements in diagnostic image quality of the mammogram especially for women with radiographically dense breasts. However, some improvement is expected for all breast imaging. The axilla-inferior rotation for the mediolateral oblique views will have the most benefit for women where the axillary tissue or the inferior main breast tissue are not adequately compressed using a conventional compression system.

The additional spreading of breast anatomy from the increased compression results in the reduction of superposition of normal breast structures. These superimposed normal structures, called structured noise, may obscure the visibility of a cancer within the breast. An improvement in mammography image quality may also result from decreased scattered radiation and increased penetration of low energy x-rays in the areas in which compression is increased. These factors may result in improved contrast and signal-to-noise of masses, lesions, calcifications or other potential abnormalities.

A further advantage of the present system is a reduced radiation dose. The reduction in dose depends on the location of the most radiographically dense region of the breast. The automatic exposure detector, which determines the radiation dose, is generally placed under the most radiographically dense area of the breast. If the most radiographically dense area is near the chest wall, the radiation dose will remain essentially the same because this area will be compressed to approximately the same thickness. If the most radiographically dense area is near the nipple or in the mid breast, some reduction of breast dose is expected because the breast is more compressed in these areas and, thus, penetrated with less radiation dose.

Another advantage of the present invention, is the substantially uniform or equal compression force for the entire breast.

BRIEF DESCRIPTION OF THE DRAWINGS

FIGS. 5a and 5b illustrate the placement of radiation detectors for the mediolateral oblique view and the craniocaudal view, FIGS. 6a and 6b illustrate an embodiment of the invention having axilla-inferior rotation.

DETAILED DESCRIPTION OF THE INVENTION

Figure 1:
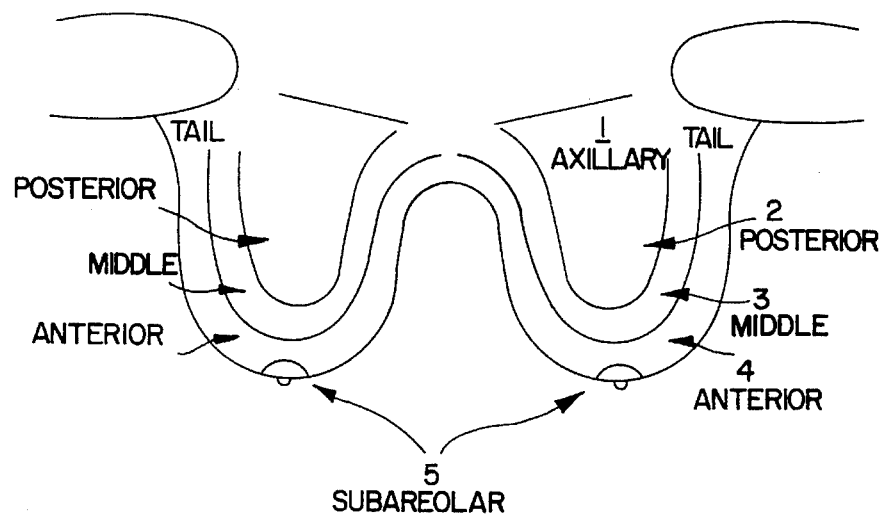
FIG. 1 illustrates the regions of the breast.
Figure 2A:
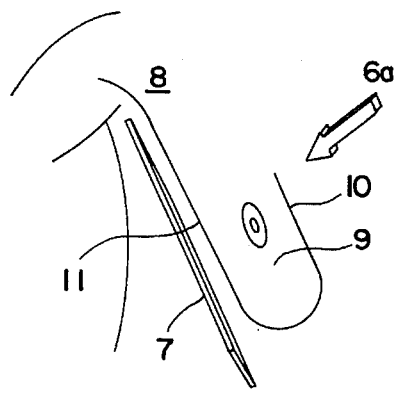
FIG. 2a illustrates the mediolateral oblique view of a breast.
Figure 2B:
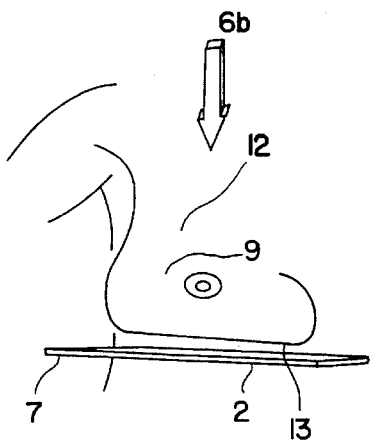
FIG. 2b illustrates the craniocaudal view of a breast.
Figure 3:
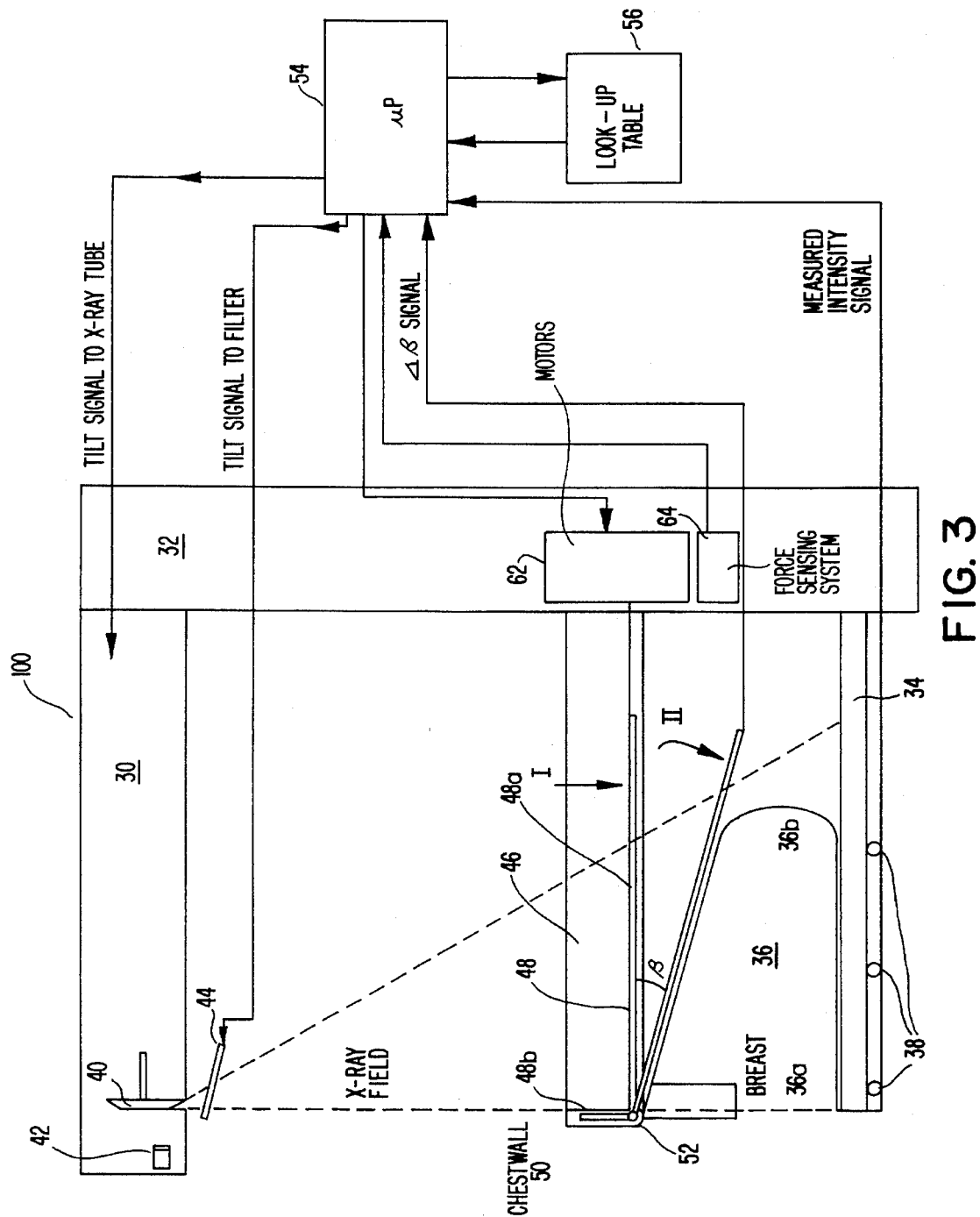
FIG. 3 illustrates a first embodiment of the compression device of the present invention and operation thereof.

Referring to FIG. 3, a mammogram system 100 comprising an x-ray tube 30 connected to a system arm 32 is shown. A grid/detector system 34 is connected to the system arm 32 at the end opposite the x-ray tube 30. A breast 36 with a chest wall side 36a and a nipple end 36b is shown schematically resting on the grid/detector 34. Detection systems currently in use are composed of a scintillating screen and a film. (Digital detectors for mammography will soon be available.) The detector includes a plurality of radiation detectors 38 placed at different spots under the breast to detect the level of radiation. In a preferred embodiment, the radiation detectors 38 would be placed at 3 to 6 locations with one detector at the chest wall side 36a of the breast and one detector at the nipple end 36b of the breast. The x-ray tube 30 has an anode 40 and a cathode 42. The anode 40 acts as the source of x-rays. A filter 44 is located just below the x-ray tube underneath the anode 40. The filter 44 is preferably made of molybdenum or rhodium and may be either a filter of uniform thickness or a wedge filter.

Between the x-ray tube 30 and the grid/detector 34, a paddle support frame 46 and a compression paddle or plate 48 are located. The support frame 46 is slidably mounted on the system arm 32 by a mechanism (not shown) well known to those skilled in the art. The compression paddle 48 is connected to the support frame 46 at a side opposite from the system arm 32, i.e., at the chest wall 50 side of the support frame 46, by a pivot mechanism 52, such as a hinge or pin having a rotation axis which is parallel to the detector and the system arm. The chest wall is not explicitly shown in the drawings, but is indicated by the words "chest wall" and the number 50. The compression paddle 46 is comprised of two parts: a breast part 48a substantially parallel to the detector and a chest wall part 48b substantially perpendicular to the detector. The chest wall portion 48b may be hinged to the breast portion 48a, so that the chest wall portion stays perpendicular to the detector 34 when the breast wall portion 48a is rotated around pivot connection 52 towards the detector 34, as described below.

Alternatively, the compression paddle can be a unified unit without a support frame. In other words, the paddle 48 is pivotally connected directly to the system arm 32.

The compression device operates as follows. Initially, the support frame 46 and the compression paddle 48 with it are moved along the system arm 32 toward the detector 34 until the breast 36 is compressed by the paddle 48 in a substantially parallel or horizontal position to the grid/detector 34, as indicated by arrow I. The chest wall portion 48b of the compression paddle is kept perpendicular to the detector 34. After the initial desired compression is achieved, the breast portion 48a of the compression paddle is rotated downward toward the detector over the nipple or anterior breast, as indicated by arrow II, until a final desired compression of the breast is achieved. This craniocaudal rotation increases the compression toward the nipple end of the breast.

Figure 4:
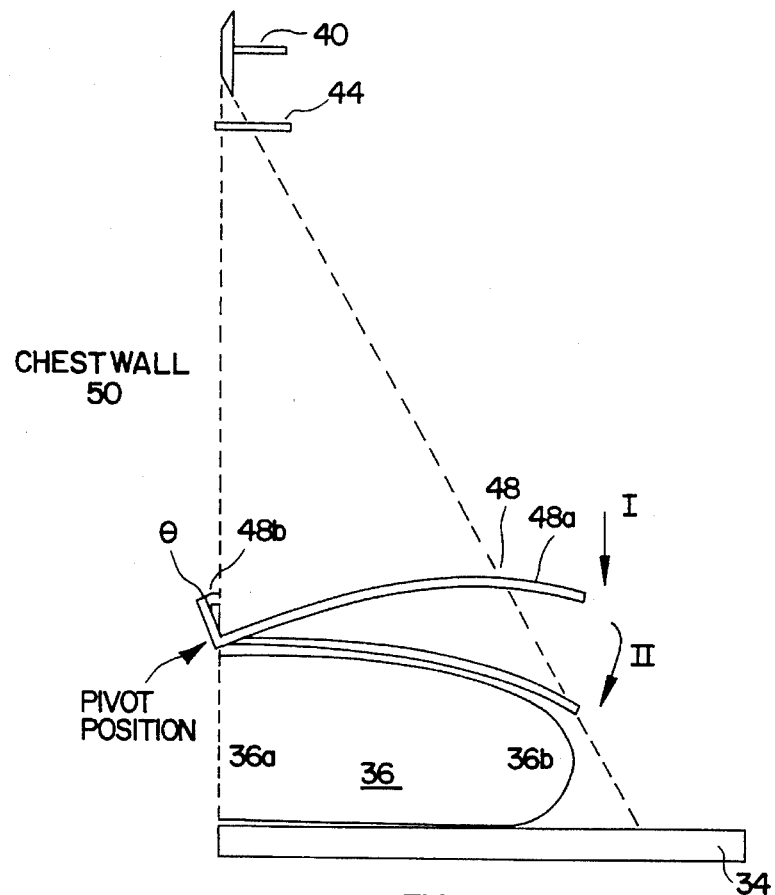
FIG. 4 illustrates another embodiment of the compression device of the present invention and operation thereof.
Figure 8A:
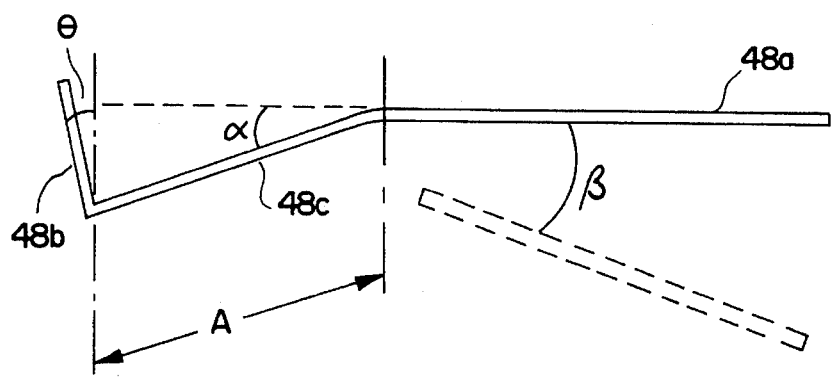
FIGS. 8a and 8b illustrate the shape and angles of movement of the compression paddle.

Another embodiment of the invention is shown in FIG. 4. In this embodiment, the compression paddle 48 comprises a contoured breast portion 48a which is shaped to follow the contours of the breast 36. In FIG. 8a, another contoured paddle is shown which comprises angled segments: an angled/curved portion 48c located between the chest wall portion 48b and breast portion 48a. Returning to FIG. 4, the chest wall portion 48b of the paddle is angled θ towards the chest wall 50 and away from the system arm 32 to form an essentially right or 90° angle with the breast portion 48a.

In operation, the compression paddle 48 is moved along the system arm 32 down toward the detector 34 over the entire breast, as indicated by arrow I. The chest wall portion 48b maintains its angle θ towards the chest wall 50 during this initial downward compression. During the initial downward compression, the contoured shape of the paddle aids in pushing the breast tissue away from the chest wall and into the imaged volume of breast tissue. Once the desired, initial compression is achieved, the contoured breast portion 48a of the paddle is rotated down towards the detector 34 over the nipple end 36b in the final compression direction, as indicated by arrow II. This last rotation can be continued until adequate compression of the entire breast is achieved. For most women, the chest wall portion 48b of the paddle becomes substantially perpendicular to the detector, i.e., angle θ is substantially zero, and the angled portion 48c of the paddle becomes substantially parallel to the detector during the rotation towards the nipple for the paddle in FIG. 8a.

An image obtained with the inventive compression device may have increased film density at the nipple end of the breast due to increased compression which decreases the breast thickness thereby allowing higher x-ray transmission. Increased film density may also occur in the axilla or inferior breast in the mediolateral oblique view. Therefore, intensity or flux of the x-rays may have to be reduced in these areas. To correct for this density gradient and to provide a uniform density from the chest wall to near the nipple, the filter 44 may be a wedge filter, the anode 40 may have a steep angle or the beam filter 44 and/or x-ray 30 tube may be tilted. These corrections would compensate for the difference in breast tissue thickness and transmitted x-ray intensity.

A conventional system for moving the x-ray tube is available from Continental X-ray. The Continental system uses a tilting x-ray tube for magnification films of the breast and a single radiation detector for AEC. It is designed to improve image sharpness, but will also result in shaping of the x-ray beam. The angle of the tube can be tilted from the normal of 16° from horizontal to 4° from the horizontal, with positions at 12° and 8° from horizontal. The system is controlled by pushbutton switches.

In one embodiment of the inventive device, the rotation of the filter and/or x-ray tube can be controlled by measuring the angulation of the compression paddle and transmitting a signal to rotate or tilt the tube and/or filter a certain amount.

The degree of rotation will be a function of both peak kilovoltage and compression plate angulation. The peak kilovoltage determines the maximum energy of the x-rays. At high kilovoltage, less beam shaping is necessary and at low kilovoltage, more beam shaping is necessary.

The tilting is accomplished by measuring the angle of rotation $\beta$ of the breast portion of the paddle 48a. A feedback device or microprocessor 54 can be used to obtain these measurements. The rotation angle $\beta$ and peak kilovoltage are correlated to obtain the necessary tilt angle for the x-ray tube and/or filter. A look-up table 56 can be used to find the tilting angle for the x-ray tube and/or filter based on the rotation angle and peak kilovoltage. A signal is then sent to the x-ray tube and/or filter to rotate them. This rotation can also be accomplished manually.

Preferably, the tilt of the x-ray tube and/or filter can be controlled by measurement of the transmitted x-ray intensity at several regions of the breast. For this purpose, radiation is detected under the breast in several locations by the radiation detectors 38 used for automatic exposure control (AEC).

Figure 5A:
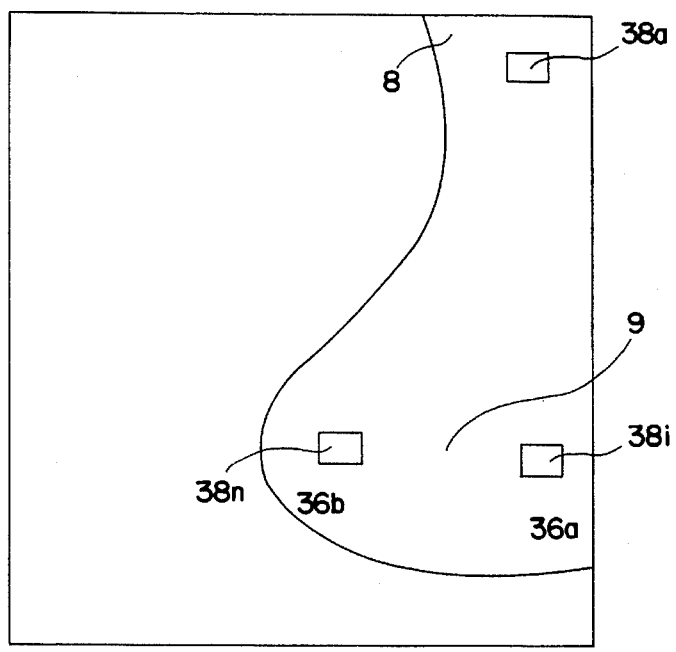

The radiation detectors are placed at locations under the breast as shown in FIGS. 5a and 5b. For the mediolateral oblique view, as shown in FIG. 5a, at least three radiation detectors 38 are used: one under the nipple or anterior end 38n, one under the axilla 38a, and one under the inferior or main lobe 38i. For the craniocaudal view, as shown in FIG. 5b, at least two radiation detectors 38 are used: one at the chest wall end of the main lobe 38c and one at the nipple end 38n. The detectors 38 are movable to adjust for different sized breasts and for views of the left or right breast. Alternatively a whole area detector can be used instead of the individual detectors.

The microprocessor 54 will send a signal to a motor to tilt the x-ray tube and/or filter based on this measured intensity. The x-ray tube and/or filter will be tilted so that the transmitted x-ray intensity is substantially equal under the breast. Alternatively, the microprocessor could insert at least one wedge filter to obtain the uniform x-ray intensity under the breast.

Figure 6B:
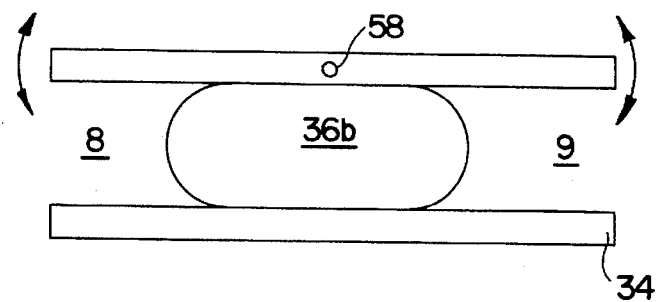

Another embodiment of the invention comprises allowing for axilla-inferior rotation of the compression paddle, as shown in FIGS. 6a and 6b. For this purpose a lockable pivot point 58 having a rotation axis substantially orthogonal to the chest wall is provided on the support frame 46. Preferably, the pivot point comprises a pin. This pivot point 58 allows for rotation of the paddle 48 in two directions: towards the armpit (axilla) or towards the inferior or the main lobe of the breast. The axilla-inferior rotation can be controlled manually or automatically. For an automatic rotation, a servo-system 62 is used to control the axilla-inferior rotation. The system may also operate by allowing the paddle to freely rotate around the pivot point 58. The paddle rotation would then be determined by the patient anatomy. FIG. 6b shows the axilla-inferior-rotation of the paddle as seen looking towards the nipple end 36b. The paddle can either rotate towards the axilla 8 or towards the main lobe or inferior breast 9.

Rotation of the compression paddle in either direction, i.e., craniocaudal or mediolateral oblique (axilla-inferior), can be controlled either manually, mechanically or with microprocessor controlled motors which are responsive to compressive forces on the breast. The motion of the compression device should be maintained such that initial compression will push the breast tissue away from the chest wall and the secondary rotation of the compression plate toward the detector will provide additional compression toward the nipple. Manual fine tuning or adjustments can be performed for any type of control. The system would respond to measured forces or pressures in order to optimize image quality and patient comfort.

The manual rotation can be accomplished with use of a lockable pivot at pivot connections 52 and 58. For the craniocaudal rotation, the pivot connection 52 is locked during the initial compression where the paddle 48 is brought down parallel to the detector 34. Then the pivot 52 is manually unlocked and the rotation of the breast portion 48a towards the detector 34 over the nipple commences. After the operator has achieved the desired compression, the pivot is locked and the exposure is taken. For the axilla-inferior rotation, the pivot 58 is either locked or unlocked. If unlocked the paddle will rotate on its own during the initial, parallel compression of the paddle. Before the exposure, manual fine tuning and locking of the pivot 58 is performed.

Figure 7:
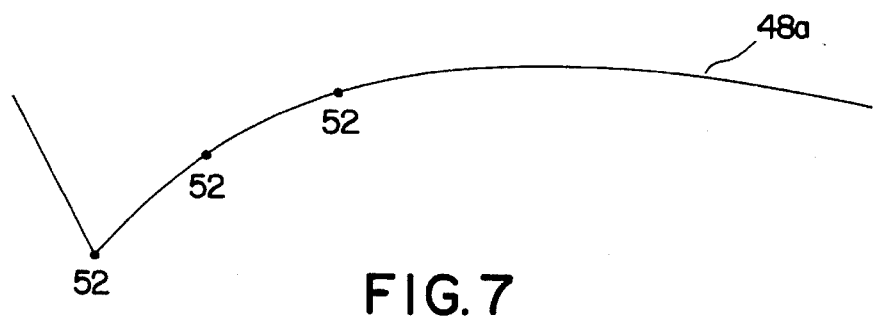
FIG. 7 illustrates various locations for the pivot connection on the compressions paddle.

During mechanically balanced control, the rotation commences when a predetermined force during the initial compression is obtained. The paddle 48 is mounted at its pivot connection 52, so that there is resistance to rotation. The amount of resistance determines the force at which the rotation towards the detector 34 over the nipple will automatically begin. Alternatively, pivot connection 52 can be located out along the breast portion 48a, away from the chest wall portion, as shown in FIG. 7. These locations will also allow the rotation of the paddle towards the detector to commence automatically upon a predetermined force being reached. Axilla-inferior rotation will also commence automatically in a similar manner. If the force is greater on one side of the breast, i.e., axilla or inferior, the paddle will rotate towards the other side.

Alternatively, the rotation of the compression paddle can be controlled by microprocessor 54 controlled motors 62, as shown in FIGS. 3 and 6a. The rotation of the paddle is controlled by the overall compressive force applied during the initial compression. This force is measured by a force sensing system 64. Such a system is known in the prior art and can be controlled by the microprocessor 54. The overall compressive force is measured by the microprocessor 54 which receives signals from the force sensing system. When the overall force reaches a predetermined value, the microprocessor 54 signals the motors 62 to commence rotation of the breast portion 48a towards the detector.

Figure 8B:
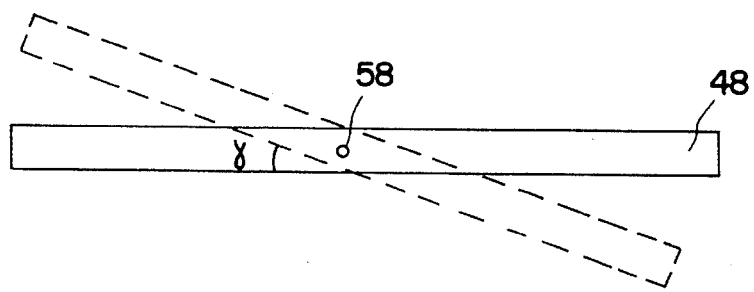

FIGS. 8a and 8b illustrate the angles of rotation for the paddle 48. In FIG. 8a, a side view of a paddle which is contoured by angled segments is illustrated. Angle $\theta$ is the angle that the chest wall portion 48b of the paddle makes with the chest wall. Angle $\alpha$ is the angle from a line parallel to the dectector of the angled portion 48c of the paddle. This angle $\alpha$ enables the paddle to push the breast tissue away from the chest wall and towards the nipple end of the breast during the initial compression movement. The angled portion 48c has a length A. Angle $\beta$ is the angle the breast portion 48a of the paddle is rotated towards the nipple end of the breast. It will be apparent that instead of being flat, the angled portion 48c and the breast portion 48a of FIG. 8a can be gently curved.

FIG. 8b, illustrates the axilla-inferior rotation of FIG. 6a with angle $\gamma$ being the angle of rotation. The paddle 48 can rotate in either direction for the axilla-inferior rotation.

Exemplary ranges for these angles using two different sized paddles are given in the following table:

| ANGLE OF ROTATION | SIZE OF PADDLE | |
|---|---|---|
| | 18 × 24 cm | 24 × 30 cm |
| θ | 12° | 12° |
| α | 12° | 12° |
| β | 0 to 16° | 0 to 16° |
| γ | ±12° or 16° | ±12° or 16° |
| A | 3 cm | 6 cm |

Finally, the above described embodiments of the present invention are intended to be illustrative only. Numerous alternative embodiments may be devised by those skilled in the art without departing from the spirit and scope of the following claims.

We claim:

1. A breast compression device for a mammography imaging system having an x-ray tube connected to a system arm and an image detector connected to said system arm at an end opposite from said x-ray tube, said breast compression device comprising,
   a paddle support frame slidably mounted on said system arm between said x-ray tube and said detector, and
   a compression paddle pivotally connected within said support frame by at least one pivot connection, said at least one pivot connection being located on a chest wall side of said support frame which is opposite said system arm, said compression paddle being substantially horizontal with respect to said detector and being rotatable about said pivot connection.

2. The device of claim 1, wherein said compression paddle comprises a breast portion substantially parallel to said detector and a chest wall portion which is substantially perpendicular to said detector.

3. The device of claim 2, wherein said compression paddle is mounted on said pivot connection at a location where said breast portion and said chest wall portion meet.

4. The device of claim 2, wherein said breast portion is contoured to mimic contours of a breast.

5. The device of claim 4, further comprising an axilla-inferior rotation pivot connection on a side of said support frame on the system arm wherein said axilla-inferior pivot connection has a rotation axis orthogonal to said system arm and parallel to said detector.

6. The device of claim 5, wherein said axilla-inferior rotation pivot connection is controlled by a servo-motor system.

7. The device of claim 4, further comprising a motor to control said rotation about said pivot connection.

8. The device of claim 7, wherein said motor is controlled by a microprocessor.

9. The device of claim 4, wherein said contoured breast portion is contoured so that breast tissue is pushed toward the dectector, out and forward toward a nipple end of a breast.

10. The device of claim 4, wherein said contoured breast portion is curved.

11. The device of claim 4, wherein said contoured breast portion comprises a plurality of angled segments.

12. The device of claim 1, wherein said compression paddle is contoured to mimic contours of a breast.

13. The device of claim 4, wherein said chest wall portion is hinged so that upon rotation of said breast portion, said chest wall portion remains perpendicular to said detector.

14. The device of claim 4, wherein said chest wall portion is angled away from said system arm to form a substantially 90° angle with said contoured breast portion.

15. The device of claim 4, wherein said pivot connection is lockable.

16. The device of claim 5, wherein said axilla-inferior rotation pivot connection is lockable.

17. The device of claim 4, wherein said paddle is mounted at the pivot connection having a resistance to rotation.

18. The device of claim 4, wherein said pivot connection is located along said breast portion away from said chest wall portion.

19. The device of claim 5, wherein said axilla-inferior pivot connection is resistant to rotation.

20. The device of claim 4, further comprising
   at least one motor connected to said paddle at said system arm,
   a force sensing system connected to said paddle for measuring exerted force, and
   a microprocessor connected to said force sensing system for receiving a measured force signal and to said motor for transmitting a signal to commence rotation of said paddle when said measured force signal is at a predetermined level.

21. A breast compression device for a mammography imaging system having an x-ray tube connected to a system arm and an image detector connected to said system arm at an end opposite from said x-ray tube, said breast compression device comprising,
   a compression paddle slidably mounted on said system arm and connected to said system arm by at least one pivot connection, said compression paddle being substantially parallel to said detector during initial compression and angled toward the detector at a side opposite said system arm during final compression.

22. A breast compression device for a mammography imaging system having an x-ray tube connected to a system arm and an image detector connected to said system arm at an end opposite from said x-ray tube, said breast compression device comprising,
   a paddle support frame slidably mounted on said system arm between said x-ray tube and said detector,
   a compression paddle connected within said support frame on a chest wall side of said support frame which is opposite said system arm, said compression paddle being substantially parallel to said detector, and
   an axilla-rotation pivot connection on a side of said support frame against said system arm, wherein said pivot connection has a rotation axis othogonal to said system arm and parallel to said detector.

23. The device of claim 22, wherein said pivot connection connects said support frame to said system arm.

24. A method of compressing breast tissue for a mammography system having an x-ray tube connected to a system arm, an image detector connected to said system arm at an end opposite from said x-ray tube and a compression paddle slidably connected to said system arm between said x-ray tube and said image detector, said method comprising,
   initially moving said compression paddle down to the breast tissue parallel to said image detector, and
   thereafter, rotating the paddle down toward said detector and around a pivot connection located at a chest wall side of said paddle.

25. The method of claim 24, wherein said compression paddle has a portion parallel to said detector and extending over the breast tissue and a portion vertical to said detector and positioned against the chest wall and said perpendicular portion remains in the same position against the chest wall during rotation of said paddle down toward said detector.

26. A method of compressing breast tissue for a mammography system having an x-ray tube connected to a system arm, an image detector connected to said system arm at an end opposite from said x-ray tube and a compression paddle movably connected to said system arm between said x-ray tube and said image detector, said method comprising, initially moving a compression paddle down to the breast tissue, wherein said compression paddle has a contoured breast portion extending over said breast tissue, and thereafter, rotating said curved breast portion down towards an anterior end of said breast tissue and around a pivot connection located at a chest wall side of said paddle until adequate and essentially uniform compression of the entire breast is achieved.

27. The method of claim 26, further comprising rotating said breast portion down towards said anterior end until an angled chest wall portion of said paddle becomes substantially perpendicular to said detector.

28. The method of claim 26, wherein the breast tissue is pushed away from the chest wall and toward an imaged tissue volume during the initial movement and the anterior end of said breast tissue is compressed during rotation of said breast portion.

29. The method of claim 28, further comprising automatically rotating said breast portion as compression force builds during said initial compression.

30. The method of claim 28, further comprising, maintaining the motion of the paddle such that the initial compression will push the breast tissue away from the chest wall and the rotation of the paddle will provide compression toward the anterior end of the breast.

31. The method of claim 28, further comprising rotating said paddle in an axilla-inferior direction.

32. The method of claim 28, further comprising automatically commencing an axilla-inferior rotation when compressive force on the axilla is not equal to compressive force on the inferior breast.

33. The method of claim 26, further comprising commencing said rotation towards said detector when a predetermined force is reached during the initial compression.

34. The method of claim 31, further comprising commencing said axilla-inferior rotation when force on the axilla is not equal to force on the inferior breast.

35. The method of claim 26, further comprising, sensing force applied during said initial compression, and automatically commencing rotation of said paddle towards said detector over the nipple when said sensed force reaches a predetermined value.

* * * * *